United States Patent
Chang et al.

(10) Patent No.: US 9,475,827 B2
(45) Date of Patent: Oct. 25, 2016

(54) TRIS(TRIMETHYL SILOXYL)SILANE VINYLIC MONOMERS AND USES THEREOF

(71) Applicants: Novartis AG, Basel (CH); Shin-Etsu Chemical Company, Ltd., Tokyo (JP)

(72) Inventors: Frank Chang, Cumming, GA (US); Mamoru Hagiwara, Akron, OH (US); Shoji Ichinohe, Gunma (JP)

(73) Assignees: SHIN-ETSU CHEMICAL COMPANY, LTD., Tokyo (JP); NOVARTIS AG, Basel (CH)

( * ) Notice: Subject to any disclaimer, the term of this patent is extended or adjusted under 35 U.S.C. 154(b) by 0 days.

(21) Appl. No.: 14/651,539

(22) PCT Filed: Dec. 13, 2013

(86) PCT No.: PCT/US2013/074921
§ 371 (c)(1),
(2) Date: Jun. 11, 2015

(87) PCT Pub. No.: WO2014/093772
PCT Pub. Date: Jun. 19, 2014

(65) Prior Publication Data
US 2015/0315213 A1    Nov. 5, 2015

Related U.S. Application Data

(60) Provisional application No. 61/737,218, filed on Dec. 14, 2012.

(51) Int. Cl.
C08L 101/14    (2006.01)
C07F 7/08    (2006.01)
C08F 287/00    (2006.01)
G02B 1/04    (2006.01)

(52) U.S. Cl.
CPC ........... *C07F 7/0834* (2013.01); *C07F 7/0854* (2013.01); *C08F 287/00* (2013.01); *G02B 1/043* (2013.01)

(58) Field of Classification Search
None
See application file for complete search history.

(56) References Cited

U.S. PATENT DOCUMENTS

| 4,136,250 A | 1/1979 | Mueller |
| 4,153,641 A | 5/1979 | Deichert |
| 4,182,822 A | 1/1980 | Chang |

(Continued)

FOREIGN PATENT DOCUMENTS

| EP | 0958315 B1 | 6/2001 |
| EP | 0932635 B1 | 7/2001 |
| EP | 0961941 B1 | 4/2002 |
| EP | 1870736 A1 | 12/2007 |
| EP | 1870737 A1 | 12/2007 |
| EP | 1870735 B1 | 3/2009 |

(Continued)

OTHER PUBLICATIONS 14651539-513253-EICSEARCH, Jun. 16, 2016.*

(Continued)

*Primary Examiner* — Peter A Salamon
(74) *Attorney, Agent, or Firm* — Jian Zhou (57) ABSTRACT

The invention provides a TRIS-containing vinylic monomer which comprises one sole (meth)acryloyloxy group and a tris(trimethylsiloxy)silyl group covalently linked to the ethylenically-unsaturated group through a polyoxyethylene linker. The present invention is also related to a polymer, an actinically-crosslinkable silicone-containing prepolymer, a silicone hydrogel polymeric material, or a silicone hydrogel contact lens, which comprises monomeric units derived from a TRIS-containing vinylic monomer of the invention. In addition, the invention provides a method for making a TRIS-containing vinylic monomer of the invention.

7 Claims, 1 Drawing Sheet

(56) References Cited

U.S. PATENT DOCUMENTS

| | | | |
|---|---|---|---|
| 4,189,546 A | 2/1980 | Deichert | |
| 4,254,248 A | 3/1981 | Friends | |
| 4,259,467 A | 3/1981 | Keogh | |
| 4,260,725 A | 4/1981 | Keogh | |
| 4,261,875 A | 4/1981 | LeBoeuf | |
| 4,276,402 A | 6/1981 | Chromecek | |
| 4,327,203 A | 4/1982 | Deichert | |
| 4,341,889 A | 7/1982 | Deichert | |
| 4,343,927 A | 8/1982 | Chang | |
| 4,355,147 A | 10/1982 | Deichert | |
| 4,444,711 A | 4/1984 | Schad | |
| 4,460,534 A | 7/1984 | Boehm | |
| 4,485,236 A | 11/1984 | Rasmussen | |
| 4,486,577 A | 12/1984 | Mueller | |
| 4,543,398 A | 9/1985 | Bany | |
| 4,605,712 A | 8/1986 | Mueller | |
| 4,661,575 A | 4/1987 | Tom | |
| 4,684,538 A | 8/1987 | Klemarczyk | |
| 4,703,097 A | 10/1987 | Wingler | |
| 4,711,943 A * | 12/1987 | Harvey, III | C07F 7/0854 523/107 |
| 4,833,218 A | 5/1989 | Lee | |
| 4,837,289 A | 6/1989 | Mueller | |
| 4,954,586 A | 9/1990 | Toyoshima | |
| 4,954,587 A | 9/1990 | Mueller | |
| 5,010,141 A | 4/1991 | Mueller | |
| 5,034,461 A | 7/1991 | Lai | |
| 5,039,761 A | 8/1991 | Ono | |
| 5,070,170 A | 12/1991 | Robertson | |
| 5,079,319 A | 1/1992 | Mueller | |
| 5,346,946 A | 9/1994 | Yokoyama | |
| 5,358,995 A | 10/1994 | Lai | |
| 5,387,632 A | 2/1995 | Lai | |
| 5,416,132 A | 5/1995 | Yokoyama | |
| 5,451,617 A | 9/1995 | Lai | |
| 5,486,579 A | 1/1996 | Lai | |
| 5,527,925 A | 6/1996 | Chabrecek | |
| 5,583,163 A | 12/1996 | Müller | |
| 5,583,244 A | 12/1996 | Uchida | |
| 5,612,389 A | 3/1997 | Chabrecek | |
| 5,612,391 A | 3/1997 | Chabrecek | |
| 5,621,018 A | 4/1997 | Chabrecek | |
| 5,658,849 A * | 8/1997 | Yamazaki | B41M 5/443 428/32.64 |
| 5,665,840 A | 9/1997 | Pohlmann | |
| 5,670,594 A * | 9/1997 | Nakada | C08F 230/08 526/279 |
| 5,712,356 A | 1/1998 | Bothe | |
| 5,760,100 A | 6/1998 | Nicolson | |
| 5,843,346 A | 12/1998 | Morrill | |
| 5,849,811 A | 12/1998 | Nicolson | |
| 5,849,841 A | 12/1998 | Mühlebach | |
| 5,894,002 A | 4/1999 | Boneberger | |
| 5,936,052 A | 8/1999 | Bothe | |
| 5,962,548 A | 10/1999 | Vanderlaan | |
| 5,981,675 A | 11/1999 | Valint, Jr. | |
| 6,039,913 A | 3/2000 | Hirt | |
| 6,043,328 A | 3/2000 | Domschke | |
| 6,165,408 A | 12/2000 | Steinmann | |
| 6,221,303 B1 | 4/2001 | Steinmann | |
| 6,303,687 B1 | 10/2001 | Müller | |
| 6,342,570 B1 | 1/2002 | Bothe | |
| 6,472,489 B1 | 10/2002 | Stockinger | |
| 6,479,587 B1 | 11/2002 | Stockinger | |
| 6,492,478 B1 | 12/2002 | Steinmann | |
| 6,627,124 B1 | 9/2003 | Herbrechtsmeier | |
| 6,762,264 B2 | 7/2004 | Künzler | |
| 6,800,225 B1 | 10/2004 | Hagmann | |
| 6,867,245 B2 | 3/2005 | Iwata | |
| 7,091,283 B2 | 8/2006 | Müller | |
| 7,238,750 B2 | 7/2007 | Müller | |
| 7,268,189 B2 | 9/2007 | Müller | |
| 7,384,590 B2 | 6/2008 | Kelly | |
| 7,387,759 B2 | 6/2008 | Kelly | |
| 7,521,519 B1 | 4/2009 | Hirt | |
| 7,566,754 B2 | 7/2009 | Müller | |
| 7,956,135 B2 | 6/2011 | Hirt | |
| 8,044,111 B2 | 10/2011 | Chang | |
| 8,048,968 B2 | 11/2011 | Phelan | |
| 8,071,658 B2 | 12/2011 | Zhou | |
| 8,071,696 B2 | 12/2011 | Hirt | |
| 8,071,703 B2 | 12/2011 | Zhou | |
| 8,211,955 B2 | 7/2012 | Chang | |
| 8,263,679 B2 | 9/2012 | Zhou | |
| 8,263,720 B1 * | 9/2012 | Salamone | A61L 26/0019 424/443 |
| 8,283,429 B2 | 10/2012 | Zhou | |
| 8,367,746 B2 | 2/2013 | Manesis | |
| 8,614,261 B2 | 12/2013 | Iwata | |
| 2004/0082680 A1 | 4/2004 | Phelan | |
| 2004/0249180 A1 * | 12/2004 | Nakamura | C07F 7/0852 556/443 |
| 2005/0113549 A1 | 5/2005 | Devlin | |
| 2006/0063852 A1 | 3/2006 | Iwata | |
| 2007/0066706 A1 | 3/2007 | Manesis | |
| 2007/0296914 A1 | 12/2007 | Hong | |
| 2008/0015315 A1 | 1/2008 | Chang | |
| 2008/0143003 A1 | 6/2008 | Phelan | |
| 2008/0143958 A1 | 6/2008 | Medina | |
| 2008/0231798 A1 | 9/2008 | Zhou | |
| 2008/0234457 A1 | 9/2008 | Zhou | |
| 2009/0085001 A1 * | 4/2009 | Furuta | C08F 220/24 252/8.62 |
| 2010/0120939 A1 | 5/2010 | Phelan | |
| 2010/0296049 A1 | 11/2010 | Justynska | |
| 2010/0298446 A1 | 11/2010 | Chang | |
| 2011/0063567 A1 | 3/2011 | Domschke | |
| 2012/0029111 A1 | 2/2012 | Chang | |
| 2012/0088843 A1 | 4/2012 | Chang | |
| 2012/0088844 A1 | 4/2012 | Kuyu | |
| 2012/0088861 A1 | 4/2012 | Huang | |
| 2012/0252925 A1 | 10/2012 | Iwata | |
| 2015/0315213 A1 * | 11/2015 | Chang | C07F 7/0854 523/107 |

FOREIGN PATENT DOCUMENTS

| | | |
|---|---|---|
| EP | 1243960 B2 | 10/2013 |
| WO | 00/31150 A1 | 6/2000 |

OTHER PUBLICATIONS

Authors: Chloé Giardi, Vincent Lapinte, Francoise Nielloud, Jean-Marie Devoisselle and Jean-Jacques Robin Title: Synthesis of Polyoxazolines Using Glycerol Carbonate Derivative and End Chains Functionalization via Carbonate and Isocyanate Routes Published: Journal of Polymer Science: Part A: Polymer Chemistry 48 (2010) pp. 4027-4035.

Authors: Leendert W. Schwab, Renee Kroon, Arend Jan Schouten and Katja Loos Title: Enzyme-Catalyzed Ring-Opening Polymerization of Unsubstituted B-Lactam Published: Macromolecular Rapid Communications, 2008, vol. 29, pp. 1-26.

Authors: Lisa M. Muratore, Johan P.A. Heuts and Thomas P. Davis Title: Synthesis of 3-[tris(trimethylsilyloxy)silyl]propyl methacrylate macromers using catalytic chain transfer polymerization: a kinetic and mechanistic study. Published: Macromolecular Chemistry and Physics, (2000) vol. 201, No. 9, p. 985-994.

PCT International Search Report dated Feb. 27, 2014, International Application No. PCT/US2013/074921, International Filing Date, Dec. 13, 2013.

PCT Written Opinion of the International Searching Authority dated Feb. 27, 2014, International Application No. PCT/US2013/074921, International Filing Date, Dec. 13, 2013.

Authors: Christine Weber, C. Remzi Becer, Anja Baumgaertel, Richard Hoogenboom and Ulrich S. Schubert Title: Preparation of Methacrylate End-Functionalized Poly(2-ethyl-2-oxazoline) Macromonomers Published: Designed Monomers and Polymers (2009) vol. 12, pp. 149-165.

* cited by examiner

TRIS(TRIMETHYL SILOXYL)SILANE VINYLIC MONOMERS AND USES THEREOF

The present invention is related to a class of tris(trimethyl siloxy)silane vinylic monomers with a polyoxyethylene segment and their uses in making medical devices including contact lenses. In addition, the present invention is related to a method for producing this class of tris(trimethyl siloxy) silane vinylic monomers.

BACKGROUND

A vinylic monomer having a tris(trimethylsilyloxy)silyl ("TRIS") group, such as, for example, tris(trimethylsilyloxy)silylpropyl acrylate, tris(trimethylsilyloxy)-silylpropyl methacrylate, tris(trimethylsilyloxy)-silylpropyl acrylamide, tris(trimethylsilyloxy)-silylpropyl methacrylamide, tris-(trimethylsiloxysilyl) propylvinyl carbamate, or the like, has been widely used in making silicone hydrogel contact lenses, as it can enhance the oxygen permeability of a lens material while giving the lens with clarity and superior lens properties. Moreover, presence of TRIS-containing vinylic monomers may also be important for dissipation of lens folding mark during lens handling. However, most of TRIS-containing vinylic monomers used in the contact lens industry and/or on the market are generally hydrophobic, not compatible with the hydrophilic components of a silicone hydrogel lens formulation, and not suitable for making water-based silicone hydrogel lens formulations. In addition, unpolymerized TRIS-containing vinylic monomers must be removed from molded lenses by using an organic solvent in a lens extraction process. Such lens extraction process increases the production cost and is not environmentally friendly.

Therefore, there is still a need for TRIS-containing vinylic monomers which have adequate solubility in water and can be used in an environmentally-friendly lens production process.

SUMMARY OF THE INVENTION

In one aspect, the invention provides a TRIS-containing vinylic monomer, which comprises one sole ethylenically unsaturated group and a tris(trimethylsilyloxy)silyl group covalently linked to the ethylenically-unsaturated group through a polyoxyethylene linker.

The present invention, in another aspect, provides a polymer which is a polymerization product of a polymerizable composition comprising a TRIS-containing vinylic monomer of the invention.

The present invention, in a further aspect, provides a method for producing a TRIS-containing vinylic monomer of the invention. The method comprises the steps of reacting a polyoxyethylene (meth)acrylate with an isocyanatoalkyl tris(trimethylsiloxy)silane, in the presence or absence of a solvent and in the presence of a catalyst.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"About" as used herein means that a number referred to as "about" comprises the recited number plus or minus 1-10% of that recited number.

A "medical device" refers to a device having surfaces that contact tissue, blood, or other bodily fluids of patients in the course of their operation. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; and (4) ophthalmic devices.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" or "hydrogel material" refers to a polymeric material which is insoluble in water, but can absorb at least 10 percent by weight of water when it is fully hydrated.

A "silicone hydrogel" refers to a silicone-containing hydrogel obtained by copolymerization of a polymerizable composition comprising at least one silicone-containing monomer or at least one crosslinkable silicone-containing prepolymer.

"Hydrophilic," as used herein, describes a material or portion thereof that will more readily associate with water than with lipids.

A "vinylic monomer" refers to a compound that has one sole ethylenically unsaturated group and is soluble in a solvent.

The term "soluble", in reference to a compound or material in a solvent, means that the compound or material can be dissolved in the solvent to give a solution with a concentration of at least about 1% by weight at room temperature (i.e., a temperature of about 20° C. to about 30° C.).

The term "insoluble", in reference to a compound or material in a solvent, means that the compound or material can be dissolved in the solvent to give a solution with a concentration of less than 0.005% by weight at room temperature (as defined above).

As used in this application, the term "ethylenically unsaturated group" is employed herein in a broad sense and is intended to encompass any groups containing at least one >C=C<group. Exemplary ethylenically unsaturated groups include without limitation (meth)acryloyl allyl, vinyl, styrenyl, or other C=C containing groups.

As used in this application, the term "(meth)acrylamide" refers to methacrylamide and/or acrylamide and the term "(meth)acrylate" refers to methacrylate and/or acrylate.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV irradiation, ionizing radiation (e.g. gamma ray or X-ray irradiation), microwave irradiation, and the like. Thermal curing or actinic curing methods are well-known to a person skilled in the art.

As used in this application, the term "hydrophilic vinylic monomer" refers to a vinylic monomer capable of forming a homopolymer that is water-soluble or can absorb at least 10 percent by weight of water at room temperature.

As used in this application, the term "hydrophobic vinylic monomer" refers to a vinylic monomer which as a homopolymer typically yields a polymer that is insoluble in water and can absorb less than 10 percent by weight of water at room temperature.

As used in this application, "TRIS" refers to a radical of —Si—[OSi(CH$_3$)$_3$]$_3$, namely the tris(trimethylsilyloxy)silyl group.

A "prepolymer" refers to a starting polymer which contains two or more ethylenically unsaturated groups and can be cured (e.g., crosslinked) actinically or thermally to obtain a crosslinked polymer having a molecular weight much higher than the starting polymer.

As used in this application, the term "crosslinker" refers to a compound or a polymer having at least two ethylenically unsaturated groups and being soluble in a solvent at room temperature. A "crosslinking agent" refers to a crosslinker having a molecular weight of about 700 Daltons or less.

A "polysiloxane" refers to a compound containing one sole polysiloxane segment of in which $R_3$, $R_4$, $R_5$, $R_6$, $R_7$, $R_8$, $R_9$, and $R_{10}$, independently of one another, are $C_1$-$C_{10}$ alkyl, $C_1$-$C_4$ alkyl- or $C_1$-$C_4$-alkoxy-substituted phenyl, $C_1$-$C_{10}$ fluoroalkyl, $C_1$-$C_{10}$ fluoroether, $C_6$-$C_{18}$ aryl radical, -alk-(OCH$_2$CH$_2$)$_{n1}$—OR$_{11}$ in which alk is $C_1$-$C_6$-alkylene divalent radical, $R_{11}$ is hydrogen or $C_1$-$C_5$ alkyl and n1 is an integer from 1 to 10, m1 and m2 independently of each other are an integer of from 0 to 50 and (m1+m2) is from 1 to 100.

A "chain-extended polysiloxane" refers to a compound containing at least two polysiloxane segments separated by a linkage.

A "polysiloxane-containing crosslinker" refers to a compound having at least two ethylenically unsaturated groups and at least one polysiloxane segment.

As used in this application, the term "polymer" means a material formed by polymerizing/crosslinking one or more monomers or prepolymers.

As used in this application, the term "molecular weight" of a polymeric material (including monomeric or macromeric materials) refers to the weight-average molecular weight unless otherwise specifically noted or unless testing conditions indicate otherwise.

The term "alkyl" refers to a monovalent radical obtained by removing a hydrogen atom from a linear or branched alkane compound. An alkyl group (radical) forms one bond with one other group in an organic compound.

The term "alkylene" or "alkane diradical" refers to a divalent radical obtained by removing one hydrogen atom from an alkyl. An alkylene group (or radical) forms two bonds with other groups in an organic compound.

The term "cycloalkane diradical" refers to a divalent radical obtained by removing two hydrogen atoms from a substituted or unsubstituted cycloalkane. A cycloalkane diradical forms two bonds with other groups in an organic compound.

In this application, the term "substituted" in reference to an alkylene divalent radical or an alkyl radical or a cycloalkane means that the alkylene divalent radical or the alkyl radical or the cycloalkane diradical comprises at least one substituent which replaces one hydrogen atom of the alkylene or alkyl radical or cycloalkane diradical and is selected from the group consisting of hydroxyl, carboxyl, —NH$_2$, sulfhydryl, $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

The term "fluid" as used herein indicates that a material is capable of flowing like a liquid.

As used herein, the term "multiple" refers to three or more.

A free radical initiator can be either a photoinitiator or a thermal initiator. A "photoinitiator" refers to a chemical that initiates free radical crosslinking/polymerizing reaction by the use of light. A "thermal initiator" refers to a chemical that initiates radical crosslinking/polymerizing reaction by the use of heat energy.

A "UV-absorbing vinylic monomer" refers to a compound comprising an ethylenically-unsaturated group and a UV-absorbing moiety which can absorb or screen out UV radiation in the range from 200 nm to 400 nm as understood by a person skilled in the art.

A "spatial limitation of actinic radiation" refers to an act or process in which energy radiation in the form of rays is directed by, for example, a mask or screen or combinations thereof, to impinge, in a spatially restricted manner, onto an area having a well defined peripheral boundary. A spatial limitation of UV radiation is obtained by using a mask or screen having a radiation (e.g., UV) permeable region, a radiation (e.g., UV) impermeable region surrounding the radiation-permeable region, and a projection contour which is the boundary between the radiation-impermeable and radiation-permeable regions, as schematically illustrated in the drawings of U.S. Pat. No. 6,800,225 (FIGS. 1-11), and U.S. Pat. No. 6,627,124 (FIGS. 1-9), U.S. Pat. No. 7,384,590 (FIGS. 1-6), and U.S. Pat. No. 7,387,759 (FIGS. 1-6), all of which are incorporated by reference in their entireties. The mask or screen allows to spatially projects a beam of radiation (e.g., UV radiation) having a cross-sectional profile defined by the projection contour of the mask or screen. The projected beam of radiation (e.g., UV radiation) limits radiation (e.g., UV radiation) impinging on a lens-forming material located in the path of the projected beam from the first molding surface to the second molding surface of a mold. The resultant contact lens comprises an anterior surface defined by the first molding surface, an opposite posterior surface defined by the second molding surface, and a lens edge defined by the sectional profile of the projected UV beam (i.e., a spatial limitation of radiation). The radiation used for the crosslinking is radiation energy, especially UV radiation, gamma radiation, electron radiation or thermal radiation, the radiation energy preferably being in the form of a substantially parallel beam in order on the one hand to achieve good restriction and on the other hand efficient use of the energy.

The intrinsic "oxygen permeability", Dk, of a material is the rate at which oxygen will pass through a material. As used in this application, the term "oxygen permeability (Dk)" in reference to a hydrogel (silicone or non-silicone) or a contact lens means a measured oxygen permeability (Dk) which is corrected for the surface resistance to oxygen flux caused by the boundary layer effect according to the procedures shown in Examples hereinafter. Oxygen permeability is conventionally expressed in units of barrers, where "barrer" is defined as $[(cm^3 \, oxygen)(mm)/(cm^2)(sec)(mm \, Hg)] \times 10^{-10}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as $[(cm^3 \, oxygen)/(cm^2)(sec)(mm \, Hg)] \times 10^{-9}$.

The term "water soluble or processable" in reference to a TRIS-containing vinylic monomer of the invention means that the vinylic monomer has a water solubility and/or dispersity of from about 1% to about 70% by weight at room temperature (about 22° C. to about 28° C.).

The term "water solubility and/or dispersity" in reference to a TRIS-containing vinylic monomer of the invention means the concentration (weight percentage) of the TRIS-containing vinylic monomer dissolved and/or dispersed in water at room temperature (about 22° C. to about 28° C.) to form a transparent aqueous solution or a slightly hazy aqueous solution having a light transmissibility of 85% or greater in the range between 400 to 700 nm.

A "coupling reaction" in this patent application is intended to describe any reaction between a pair of matching functional groups in the presence or absence of a coupling agent to form covalent bonds or linkages under various reaction conditions well known to a person skilled in the art, such as, for example, oxidation-reduction conditions, dehydration condensation conditions, addition conditions, substitution (or displacement) conditions, Diels-Alder reaction conditions, cationic crosslinking conditions, ring-opening conditions, epoxy hardening conditions, and combinations thereof.

Non-limiting examples of coupling reactions under various reaction conditions between a pair of matching co-reactive functional groups selected from the group preferably consisting of amino group (—NHR' in which R' is H or $C_1$-$C_4$ alkyl), hydroxyl group, carboxyl group, acid halide group (—COX, X=Cl, Br, or I), acid anhydrate group, aldehyde group, azlactone group, isocyanate group, epoxy group, aziridine group, and thiol group, are given below for illustrative purposes. An amino group reacts with aldehyde group to form a Schiff base which may further be reduced; an amino group —NHR' reacts with an acid chloride or bromide group or with an acid anhydride group to form an amide linkage (—CO—NR'— with R' as defined above); an amino group —NHR' reacts with an isocyanate group to form a urea linkage (—NR'—C(O)—NH— with R' as defined above); an amino group —NHR' reacts with an epoxy or aziridine group to form an amine bond (—C—NR'— with R' as defined above); an amino group —NHR' reacts (ring-opening) with an azlactone group to form an alkylene-diamido linkage (—C(O)NH-alkylene-C(O)NR'— with R' as defined above); an amino group —NHR' reacts with a carboxylic acid group in the presence of a coupling agent—carbodiimide (e.g., 1-ethyl-3-(3-dimethylaminopropyl) carbodiimide (EDC), N,N'-dicyclohexylcarbodiimide (DCC), 1-cylcohexyl-3-(2-morpholinoethyl)carbodiimide, diisopropyl carbodiimide, or mixtures thereof) to form an amide linkage; an amino group —NHR' reacts with a N-hydroxysuccinimide ester group to form an amide linkage; a hydroxyl reacts with an isocyanate to form a urethane linkage; a hydroxyl reacts with an epoxy or aziridine to form an ether linkage (—O—); a hydroxyl reacts with an acid chloride or bromide group or with an acid anhydride group to form an ester linkage; an hydroxyl group reacts with an azlactone group in the presence of a catalyst to form an amidoalkylenecarboxy linkage (—C(O)NH-alkylene-C(O)—O—); a carboxyl group reacts with an epoxy group to form an ester bond; a thiol group (—SH) reacts with an isocyanate to form a thiocarbamate linkage (—N—C(O)—S—); a thiol group reacts with an epoxy or aziridine to form a thioether linkage (—S—); a thiol group reacts with an acid chloride or bromide group or with an acid anhydride group to form a thiolester linkage; a thiol group reacts with an azlactone group in the presence of a catalyst to form a linkage (—C(O)NH—$CR_3R_4$—$(CH_2)p$-C(O)—S—). A thiol group reacts with a vinyl group based on thiol-ene reaction under thiol-ene reaction conditions to form a thioether linakge (—S—). A thiol group reacts with an acryloyl or methacryloyl group based on Michael Addition under appropriate reaction conditions to form a thioether linkage.

It is also understood that coupling agents with two reactive functional groups may be used in the coupling reactions. A coupling agent having two reactive functional groups can be a diisocyanate, a di-acid halide, a di-carboxylic acid compound, a di-acid halide compound, a di-azlactone compound, a di-epoxy compound, a diamine, or a diol. A person skilled in the art knows well to select a coupling reaction (e.g., anyone described above in this application) and conditions thereof to prepare a polysiloxane terminated with one or more ethylenically unsaturated groups. For example, a diisocyanate, di-acid halide, di-carboxylic acid, di-azlactone, or di-epoxy compound can be used in the coupling of two hydroxyl, two amino groups, two carboxyl groups, two epoxy groups, or combination thereof; a diamine or dihydroxyl compound can be used in the coupling of two isocyanate, epoxy, aziridine, carboxylic acid, acid halide or azlactone groups or combinations thereof.

Any suitable $C_4$-$C_{24}$ diisocyanates can be used in the invention. Examples of preferred diisocyanates include without limitation isophorone diisocyanate, hexamethyl-1,6-diisocyanate, 4,4'-dicyclohexylmethane diisocyanate, toluene diisocyanate, 4,4'-diphenyl diisocyanate, 4,4'-diphenylmethane diisocyanate, p-phenylene diisocyanate, 1,4-phenylene 4,4'-diphenyl diisocyanate, 1,3-bis-(4,4'-isocyanto methyl) cyclohexane, cyclohexane diisocyanate, and combinations thereof.

Any suitable diamines can be used in the invention. An organic diamine can be a linear or branched $C_2$-$C_{24}$ aliphatic diamine, a $C_5$-$C_{24}$ cycloaliphatic or aliphatic-cycloaliphatic diamine, or a $C_6$-$C_{24}$ aromatic or alkyl-aromatic diamine. A preferred organic diamine is N,N'-bis(hydroxyethyl)ethylenediamine, N,N'-dimethylethylenediamine, ethylenediamine, N,N'-dimethyl-1,3-propanediamine, N,N'-diethyl-1, 3-propanediamine, propane-1,3-diamine, butane-1,4-diamine, pentane-1,5-diamine, hexamethylenediamine, and isophorone diamine.

Any suitable diacid halides can be used in the invention. Examples of preferred diacid halide include without limitations fumaryl chloride, suberoyl chloride, succinyl chloride, phthaloyl chloride, isophthaloyl chloride, terephthaloyl chloride, sebacoyl chloride, adipoyl chloride, trimethyladipoyl chloride, azelaoyl chloride, dodecanedioic acid chloride, succinic chloride, glutaric chloride, oxalyl chloride, dimer acid chloride, and combinations thereof.

Any suitable di-epoxy compounds can be used in the invention. Examples of preferred di-epoxy compounds are neopentyl glycol diglycidyl ether, 1,4-butanediol diglycidyl ether, 1,6-hexanediol diglycidyl ether, glycerol diglycidyl ether, ethylene glycol diglycidyl ether, diethylene glycol diglycidyl ether, polyethylene glycol diglycidyl ether, propylene glycol diglycidyl ether, dipropylene glycol diglycidyl ether, and combinations thereof. Such di-epoxy compounds are available commercially (e.g., those DENACOL series di-epoxy compounds from Nagase ChemteX Corporation).

Any suitable $C_2$-$C_{24}$ diols (i.e., compounds with two hydroxyl groups) can be used in the invention. Examples of preferred diols include without limitation ethylene glycol, diethylene glycol, triethylene glycol, tetraethylene glycol, polyethylene glycol, propylene glycol, 1,4-butanediol, various pentanediols, various hexanediols, various cyclohexanediols, and combination thereof.

Any suitable $C_3$-$C_{24}$ di-carboxylic acid compounds can be used in the invention. Examples of preferred di-carboxylic acid compounds include without limitation a linear or branched $C_3$-$C_{24}$ aliphatic dicarboxylic acid, a $C_5$-$C_{24}$ cycloaliphatic or aliphatic-cycloaliphatic dicarboxylic acid, a $C_6$-$C_{24}$ aromatic or araliphatic dicarboxylic acid, a dicarboxylic acid which contains amino or imido groups or N-heterocyclic rings, and combinations thereof. Examples of suitable aliphatic dicarboxylic acids are: oxalic acid, malonic acid, succinic acid, glutaric acid, adipic acid, pimelic acid, suberic acid, azelaic acid, sebacic acid, undecanedioic acid, dodecanedioic acid, dimethylmalonic acid, octadecylsuccinic acid, trimethyladipic acid, and dimeric acids (dimerisation products of unsaturated aliphatic carboxylic acids, such as oleic acid). Examples of suitable cycloaliphatic dicarboxylic acids are: 1,3-cyclobutanedicarboxylic acid, 1,3-cyclopentanedicarboxylic acid, 1,3- and 1,4-cyclohexanedicarboxylic acid, 1,3- and 1,4-dicarboxylmethylcyclohexane, 4,4'-dicyclohexyldicarboxylic acid. Examples of suitable aromatic dicarboxylic acids are: terephthalic acid, isophthalic acid, o-phthalic acid, 1, 3-,1,4-, 2,6- or 2,7-naphthalenedicarboxylic acids, 4,4'-diphenyldicarboxylic acid, 4,4'-diphenylsulphone-dicarboxylic acid, 1,1,3-trimethyl-5-carboxyl-3-(p-carboxyphenyl)-indane, 4,4'-diphenyl ether-dicarboxylic acid, bis-p-(carboxyphenyl)-methane.

Any suitable $C_{10}$-$C_{24}$ di-azlactone compounds can be used in the invention. Examples of such diazlactone compounds are those described in U.S. Pat. No. 4,485,236 (herein incorporated by reference in its entirety).

The reactions conditions for the above described coupling reactions are taught in textbooks and are well known to a person skilled in the art.

As used in this application, the term "ethylenically functionalized" in reference to a compound or polymer or copolymer having one or more reactive functional groups (e.g., amine, hydroxyl, carboxyl, isocyanate, anhydride, and/or epoxy groups) means a process or product thereof in which one or more ethylenically unsaturated groups are covalently attached to the functional groups of the compound or polymer or copolymer by reacting an ethylenically functionalizing vinylic monomer with the compound or polymer or copolymer under coupling reaction conditions.

An "ethylenically functionalizing vinylic monomer" throughout of this patent application refers to a vinylic monomer having one reactive functional group capable of participating in a coupling (or crosslinking) reaction known to a person skilled in the art. Examples of ethylenically-functionalizing vinylic monomers include without limitation $C_2$ to $C_6$ hydroxylalkyl (meth)acrylate, $C_2$ to $C_6$ hydroxyalkyl (meth)acrylamide, allylalcohol, allylamine, amino-$C_2$-$C_6$ alkyl (meth)acrylate, $C_1$-$C_6$ alkylamino-$C_2$-$C_6$ alkyl (meth)acrylate, vinylamine, amino-$C_2$-$C_6$ alkyl (meth)acrylamide, $C_1$-$C_3$ alkylamino-$C_2$-$C_6$ alkyl (meth)acrylamide, acrylic acid, $C_1$-$C_4$ alkylacrylic acid (e.g., methacrylic ethylacrylic acid, propylacrylic acid, butylacrylic acid), N-[tris(hydroxymethyl)-methyl]acrylamide, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carobxy-4-phenyl butadiene-1,3, itaconic acid, citraconic acid, mesaconic acid, glutaconic acid, aconitic acid, maleic acid, fumaric acid, aziridinyl $C_1$-$C_{12}$ alkyl (meth)acrylate (e.g., 2-(1-aziridinyl) ethyl (meth)acrylate, 3-(1-aziridinyl) propyl (meth)acrylate, 4-(1-aziridinyl) butyl (meth)acrylate, 6-(1-aziridinyl) hexyl (meth)acrylate, or 8-(1-aziridinyl) octyl (meth)acrylate), glycidyl (meth)acrylate, vinyl glycidyl ether, allyl glycidyl ether, (meth)acryloyl halide groups ($CH_2$=CH—COX or $CH_2$=$CCH_3$—COX, X=Cl or Br), N-hydroxysuccinimide ester of (meth)acrylic acid, $C_1$ to $C_6$ isocyanatoalkyl (meth)acrylate, azlactone-containing vinylic monomers (e.g., 2-vinyl-4,4-dimethyl-1,3-oxazolin-5-one, 2-isopropenyl-4,4-dimethyl-1,3-oxazolin-5-one, 2-vinyl-4-methyl-4-ethyl-1,3-oxazolin-5-one, 2-isopropenyl-4-methyl-4-butyl-1,3-oxazolin-5-one, 2-vinyl-4,4-dibutyl-1,3-oxazolin-5-one, 2-isopropenyl-4-methyl-4-dodecyl-1,3-oxazolin-5-one, 2-isopropenyl-4,4-diphenyl-1, 3-oxazolin-5-one, 2-isopropenyl-4,4-pentamethylene-1,3-oxazolin-5-one, 2-isopropenyl-4, 4-tetramethylene-1,3-oxazolin-5-one, 2-vinyl-4,4-diethyl-1,3-oxazolin-5-one, 2-vinyl-4-methyl-4-nonyl-1,3-oxazolin-5-one, 2-isopropenyl-4-methyl-4-phenyl-1,3-oxazolin-5-one, 2-isopropenyl-4-methyl-4-benzyl-1,3-oxazolin-5-one, 2-vinyl-4,4-pentamethylene-1,3-oxazolin-5-one, and 2-vinyl-4,4-dimethyl-1,3-oxazolin-6-one, with 2-vinyl-4,4-dimethyl-1,3-oxazolin-5-one (VDMO) and 2-isopropenyl-4,4-dimethyl-1,3-oxazolin-5-one (IPDMO) as preferred zlactone-containing vinylic monomers), and combinations thereof.

In general, the invention is directed to a class of TRIS-containing vinylic monomers and uses in preparing a polymer (preferably a silicone hydrogel material), and a medical device (preferably silicone hydrogel contact lenses). A TRIS-containing vinylic monomer of the invention comprises: one sole (meth)acryloyloxy group; one sole tris(trimethylsilyloxy)silyl group; and one polyoxyethylene-containing linkage between the (meth)acryloyloxy group and the tris(trimethylsilyloxy)silyl group. A TRIS-containing vinylic monomer of the invention can be tailored to have a desired solubility (or dispersity) in a desired solvent, e.g., water or any one in a very broad range of solvents, by varying the molecular mass of polyoxyethylene segment. It can be used in a manufacturing process for making silicone hydrogel contact lenses in a more environmentally-friendly manner (e.g., using a water-based lens formulation and/or using water as solvent in lens extraction process).

The present invention, in one aspect, provides a TRIS-containing vinylic monomer being represented by formula (I)

in which: q1 is an integer of from 6 to 20; $R_1$ is hydrogen or methyl; $R_2$ is a diradical of an alkane or cycloalkane which comprises up to 20 carbon atoms and may have one or more ether, thio, amine, carbonyl, or amido linkages in the main chain.

A TRIS-containing vinylic monomers of formula (I) can be prepared from a polyoxyethylene (meth)acrylate and an isocyanatoalkyl tris(trimethyl siloxy)silane. The hydroxyl group of a polyoxyethylene (meth)acrylate ($CH_2$=CH—CO—($OCH_2CH_2$)$_n$—OH or $CH_2$=$CCH_3$—CO—($OCH_2CH_2$)$_n$—OH) can react with the isocyanate group of an isocyanatoalkyl tris(trimethyl siloxy)silane, in the presence of a catalyst (e.g., amine catalyst, such as triethylamine; tin catalysts, such as dibutyltin dilaurate; iro catalysts, such as tris(2,4-pentanedionate iron(III); or the like) to form a urethane linkage, as described below.

In a preferred embodiment, a TRIS-containing vinylic monomer of formula (I) has a water solubility or dispersibility of at least about 5%, preferably at least about 10%, more preferably at least about 20% by weight in water.

A TRIS-containing vinylic monomer of formula(I) as defined above can find use in preparing a polymer, preferably a silicone-containing actinically-crosslinkable prepolymer or a silicone hydrogel polymeric material, which is another aspect of the invention.

In another aspect, the invention is related to a polymer comprising monomeric units derived from a TRIS-containing vinylic monomer of formula (I) as defined above.

In this aspect of the invention, a polymer can be a copolymer soluble or insoluble in a solvent, preferably an actinically-crosslinkable prepolymer or a silicone hydrogel material.

A person skilled in the art knows how to prepare a polymer, an actinically-crosslinkable silicone-containing prepolymer, or a silicone hydrogel material from a polymerizable composition according to any known free-radical polymerization mechanism. The polymerizable composition for preparing a polymer, an actinically-crosslinkable silicone containing prepolymer (i.e., an intermediary copolymer for the prepolymer), or a silicone hydrogel polymeric material of the invention can be a melt, a solventless liquid in which all necessary components are blended together, or a solution in which all necessary component is dissolved in an inert solvent, such as water, an organic solvent, or mixture thereof, as known to a person skilled in the art.

Example of suitable solvents includes without limitation, water, tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimetyl ether, polyethylene glycols, polypropylene glycols, ethyl acetate, butyl acetate, amyl acetate, methyl lactate, ethyl lactate, i-propyl lactate, methylene chloride, 2-butanol, 1-propanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl, alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, t-amyl alcohol, isopropanol, 1-methyl-2-pyrrolidone, N,N-dimethylpropionamide, dimethyl formamide, dimethyl acetamide, dimethyl propionamide, N-methyl pyrrolidinone, and mixtures thereof.

The copolymerization of a polymerizable composition for preparing a polymer, an actinically-crosslinkable silicone containing prepolymer (i.e., an intermediary copolymer for the prepolymer), or a silicone hydrogel polymeric material of the invention may be induced photochemically or thermally.

Suitable photoinitiators are benzoin methyl ether, diethoxyacetophenone, a benzoylphosphine oxide, 1-hydroxycyclohexyl phenyl ketone and Darocur and Irgacure types, preferably Darocur 1173®, Irgacure 369®, Irgacure 379®, and Irgacure 2959®. Examples of benzoylphosphine oxide initiators include 2,4,6-trimethylbenzoyldiphenylophosphine oxide (TPO); bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers.

Suitable thermal polymerization initiators are known to the skilled artisan and comprise, for example peroxides, hydroperoxides, azo-bis(alkyl- or cycloalkylnitriles), persulfates, percarbonates or mixtures thereof. Examples are benzoylperoxide, tert.-butyl peroxide, di-tert.-butyl-diperoxyphthalate, tert.-butyl hydroperoxide, azo-bis(isobutyronitrile) (AIBN), 1,1-azodiisobutyramidine, 1,1'-azo-bis(1-cyclohexanecarbonitrile), 2,2'-azo-bis(2,4- dimethylvaleronitrile) and the like. The polymerization is carried out conveniently in an above-mentioned solvent at elevated temperature, for example at a temperature of from 25 to 100° C. and preferably 40 to 80° C. The reaction time may vary within wide limits, but is conveniently, for example, from 1 to 24 hours or preferably from 2 to 12 hours. It is advantageous to previously degas the components and solvents used in the polymerization reaction and to carry out said copolymerization reaction under an inert atmosphere, for example under a nitrogen or argon atmosphere.

Generally, a polymer of the invention is obtained by polymerizing thermally or actinically a polymerizable composition including a TRIS-containing vinylic monomer of formula (I) as defined above and one or more polymerizable components selected from the group consisting of a hydrophilic vinylic monomer, a hydrophobic vinylic monomer, a polysiloxane-containing vinylic monomer, a polysiloxane-containing crosslinker, a non-silicone crosslinker, a hydrophilic prepolymer, a UV-absorbing vinylic monomer, and combinations thereof. Various embodiments of all of the above-described polymerizable components are discussed below.

In accordance with the invention, any suitable hydrophilic vinylic monomers can be used in a polymerizable composition for preparing a polymer of the invention. Examples of preferred hydrophilic vinylic monomers include without limitation N-vinylpyrrolidone, N,N-dimethyl (meth)acrylamide, (meth)acrylamide, hydroxylethyl (meth)acrylamide, hydroxyethyl (meth)acrylate, glycerol methacrylate (GMA), polyethylene glycol (meth)acrylate, polyethylene glycol $C_1$-$C_4$-alkyl ether (meth)acrylate having a weight average molecular weight of up to 1500, N-vinyl formamide, N-vinyl acetamide, N-vinyl isopropylamide, N-vinyl-N-methyl acetamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, (meth)acrylic acid, ethylacrylic acid, and combinations thereof.

Any suitable hydrophobic vinylic monomers can be used in a polymerizable composition for making a polymer of the invention. By incorporating a certain amount of hydrophobic vinylic monomer in a monomer mixture, the mechanical properties (e.g., modulus of elasticity) of the resultant polymer may be improved. Examples of preferred hydrophobic vinylic monomers include methylacrylate, ethyl-acrylate, propylacrylate, isopropylacrylate, cyclohexylacrylate, 2-ethylhexylacrylate, methylmethacrylate, ethylmethacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate.

Any suitable polysiloxane-containing vinylic monomer (each comprising at least one polysiloxane segment and one sole ethylenically unsaturated group) can be used in a polymerizable composition for preparing a polymer of the invention. Preferred examples of such vinylic monomers are mono-(meth)acrylated polydimethylsiloxanes of various molecular weight (e.g., mono-3-methacryloxypropyl terminated, mono-$C_1$-$C_4$ alkyl terminated polydimethylsiloxane, or mono-(3-methacryloxy-2-hydroxypropyloxy)propyl terminated, mono-$C_1$-$C_4$ alkyl terminated polydimethylsiloxane). Alternatively, monoethylenically functionalized polysiloxanes can be obtained by ethylenically functionalizing of a monofunctionalized polysiloxanes (i.e., with one sole terminal functional group, such as, e.g., —$NH_2$, —OH, —COOH, epoxy group, halide, etc.) as described above. Suitable monofunctionalized polysiloxanes are commercially available, e.g., from Aldrich, ABCR GmbH & Co., Fluorochem, or Gelest, Inc, Morrisville, Pa.

Any suitable polysiloxane-containing crosslinkers (each of which comprises at least one polysiloxane segment and at least two ethylenically unsaturated groups) can be used in a polymerizable composition for preparing a polymer of the invention. Examples of polysiloxane-containing crosslinkers include without limitation, bis-(meth)acrylated polydimethylsiloxanes; bis-vinyl carbonate-terminated polydimethylsiloxanes; bis-vinyl carbamate-terminated polydimethylsiloxane; bis-vinyl terminated polydimethylsiloxanes; bis-(meth)acrylamide-terminated polydimethylsiloxanes; bis-3-methacryloxy-2-hydroxypropyloxypropyl polydimethylsiloxane; N,N,N',N'-tetrakis(3-methacryloxy-2-hydroxypropyl)-alpha,omega-bis-3-aminopropyl-polydimethylsiloxane; polysiloxane or chain-extended polysiloxane crosslinkers selected from the group consisting of Macromer A, Macromer B, Macromer C, and Macromer D described in U.S. Pat. No. 5,760,100 (herein incorporated by reference in its entirety); the reaction products of glycidyl (meth)acrylate with bis-aminoalkyl-terminated or bis-hydroxyalkoxyalkyl terminated polydimethylsiloxanes; the reaction products of hydroxy-containing or amino-containing vinylic monomer with bis-epoxyalkoxyalkyl-terminated polydimethylsiloxanes; polysiloxane-containing crosslinkers disclosed in U.S. Pat. Nos. 4,136,250, 4,153,641, 4,182,822, 4,189,546, 4,259,467, 4,260,725, 4,261,875, 4,343,927, 4,254,248, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,962,548, 5,981,675, 6,039,913, 6,762,264, 7,091,283, 7,238,750, 7,268,189, 7,566,754, 7,956,135, 8,071,696, 8,071,703, 8,071,658, 8,048,968, 8,283, 429, 8,263,679, 8,044,111, and 8,211,955 and in published US patent application Nos. 2008/0015315 A1, 2010/0120939 A1, 2010/0298446 A1, 2010/0296049 A1, 2011/0063567 A1, 2012/0088843 A1, 2012/0088844 A1, 2012/0029111 A1, and 2012/0088861 A1 (herein incorporated by reference in their entireties).

Any suitable non-silicone crosslinkers can be used in a polymerizable composition for preparing a polymer of the invention. Examples of preferred non-silicone crosslinkers include without limitation tetraethyleneglycol di-(meth) acrylate, triethyleneglycol di -(meth)acrylate, ethyleneglycol di-(meth)acrylate, diethyleneglycol di-(meth)acrylate, bisphenol A dimethacrylate, vinyl methacrylate, ethylenediamine di(meth)acrylamide, glycerol dimethacrylate, allyl (meth)acrylate, N,N'-methylenebis(meth)acrylamide, N,N'-ethylenebis(meth)acrylamide, N,N'-dihydroxyethylene bis (meth)acrylamide, a product of diamine (preferably selected from the group consisting of N,N'-bis(hydroxyethyl)-ethylenediamine, N,N'-dimethylethylenediamine, ethylenediamine, N,N'-dimethyl-1,3-propanediamine, N,N'-diethyl-1, 3-propanediamine, propane-1,3-diamine, butane-1,4-diamine, pentane-1,5-diamine, hexamethylenediamine, isophorone diamine, and combinations thereof) and epoxy-containing vinylic monomer (preferably selected from the group consisting of glycidyl (meth)acrylate, vinyl glycidyl ether, allyl glycidyl ether, and combinations thereof), combinations thereof. A more preferred crosslinker to be used in the preparation of a polymer, an actinically-crosslinkable silicone containing prepolymer, or a silicone hydrogel polymeric material of the invention is a hydrophilic crosslinker selected from the group consisting of tetra(ethyleneglycol) diacrylate, tri(ethyleneglycol) diacrylate, ethyleneglycol diacrylate, di(ethyleneglycol) diacrylate, glycerol dimethacrylate, allyl(meth)acrylate, N,N'-methylene bis(meth)acrylamide, N,N'-ethylene bis(meth)acrylamide, N,N'-dihydroxyethylene bis(meth)acrylamide, and combinations thereof.

Examples of hydrophilic prepolymers with multiple acryloyl or methacryloyl groups include, but are not limited to, a water-soluble crosslinkable poly(vinyl alcohol) prepolymer described in U.S. Pat. Nos. 5,583,163 and 6,303,687; a water-soluble vinyl group-terminated polyurethane prepolymer described in U.S. Patent Application Publication No. 2004/0082680; derivatives of a polyvinyl alcohol, polyethyleneimine or polyvinylamine, which are disclosed in U.S. Pat. No. 5,849,841; a water-soluble crosslinkable polyurea prepolymer described in U.S. Pat. No. 6,479,587 and in U.S. Published Application No. 2005/0113549; crosslinkable polyacrylamide; crosslinkable statistical copolymers of vinyl lactam, MMA and a comonomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635 and U.S. Pat. No. 6,492,478; branched polyalkylene glycol-urethane prepolymers disclosed in EP 958,315 and U.S. Pat. No. 6,165,408; polyalkylene glycol-tetra(meth)acrylate prepolymers disclosed in EP 961,941 and U.S. Pat. No. 6,221,303; and crosslinkable polyallylamine gluconolactone prepolymers disclosed in International Application No. WO 2000/31150 and U.S. Pat. No. 6,472,489.

Any suitable UV-absorbing vinylic monomers can be used in a polymerizable composition for preparing a polymer of the invention. Preferred UV absorbing vinylic monomers include without limitation 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl)benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxyethylphenyl)benzotriazole, 2-(2'-hydroxy-5'-methacryloxypropylphenyl) benzotriazole, 2-hydroxy-4-acryloxy alkoxy benzophenone, 2-hydroxy-4-methacryloxy alkoxy benzophenone, allyl-2-hydroxybenzophenone, 2-hydroxy-4-methacryloxy benzophenone. In accordance with the invention, the polymerizable composition comprises about 0.2% to about 5.0%, preferably about 0.3% to about 2.5%, more preferably about 0.5% to about 1.8%, by weight of a UV-absorbing agent.

In a preferred embodiment, a polymer of the invention is a silicone-containing actinically-crosslinkable prepolymer, which preferably comprises: (1) monomeric units derived from a TRIS-containing vinylic monomer of formula (I) as defined above; (2) crosslinking units derived from at least one polysiloxane-containing crosslinker as described above and/or polysiloxane units derived from a polysiloxane-containing vinylic monomer as described above; (3) hydrophilic units derived from at least one hydrophilic vinylic monomer as described above; (4) polymerizable units derived from a chain transfer agent having a first reactive functional group other than thiol group and/or a vinylic monomer having a second reactive functional group other than ethylenically-unsaturated group, wherein the polymerizable units each comprise an ethylenically unsaturated group covalently attached to one polymerizable unit through the first or second reactive functional group; (5) optionally non-silicone crosslinking units derived from at least one non-silicone crosslinker as described above; and (6) optionally UV-absorbing units derived from a UV-absorbing vinylic monomer as described above. Such a prepolymer is capable of being actinically crosslinked, in the absence of one or more vinylic monomers, to form a silicone hydrogel contact lens having a water content of from about 20% to about 75% (preferably from about 25% to about 70%, more preferably from about 30% to about 65%) by weight when fully hydrated, and an oxygen permeability (Dk) of at least about 40 barrers (preferably at least about 50 barrers, more preferably at least about 60 barrers, and even more preferably at least about 70 barrers). Preferably, such a prepolymer is water soluble or processable and has a high water solubility or dispersibility of at least about 5%, preferably at least about 10%, more preferably at least about 20% by weight in water. An actinically-crosslinkable silicone-containing prepolymer of the invention can find particular use in preparing silicone hydrogel ophthalmic lenses, in particular contact lenses.

Such a prepolymer is obtained by first polymerizing a polymerizable composition including all polymerizable components specified above, to form an intermediary copolymer and then by ethylenically functionalizing the intermediary copolymer with an ethylenically functionalizing vinylic monomer having a third reactive functional group capable of reacting with the first and/or second reactive functional group to form a linkage in a coupling reaction in the presence or absence of a coupling agent to form the prepolymer, wherein the first, second and third reactive functional groups independent of one another are selected from the group consisting of amino group, hydroxyl group, carboxyl group, acid halide group, azlactone group, isocyanate group, epoxy group, aziridine group, and combination thereof. The general procedures for preparing amphiphilic prepolymers are disclosed in U.S. Pat. Nos. 6,039,913, 6,043,328, 7,091,283, 7,268,189 and U.S. Pat. Nos. 7,238,750, 7,521,519, 8,071,703, 8,044,111, and 8,048,968; in US patent application publication Nos. US 2008-0015315 A1, US 2008-0143958 A1, US 2008-0143003 A1, US 2008-0234457 A1, US 2008-0231798 A1, 2010/0120939 A1, 2010/0298446 A1, 2012/0088843 A1, 2012/0088844 A1, and 2012/0088861 A1; all of which are incorporated herein by references in their entireties.

In accordance with the invention, the polymerizable units each comprise a basic monomeric unit being a part of a polymer chain of the prepolymer and a pendant or terminal, ethylenically-unsaturated group attached thereon, wherein each basic monomeric unit is derived from a first ethylenically functionalizing vinylic monomer having a second reactive functional group, wherein the pendant or terminal ethylenically unsaturated group is derived from a second ethylenically functionalizing vinylic monomer having a third reactive functional group which reacts with one second reactive functional in the presence or absence of a crosslinking agent to form a covalent linkage. The second and third reactive functional groups are selected from the group consisting of amino group, hydroxyl group, carboxyl group, azlactone group, isocyanate group, epoxy group, aziridine group, acid chloride, and combination thereof. Examples of such vinylic monomers are those ethylenically functionalizing vinylic monomers described above. Preferably, the first ethylenically functionalizing vinylic monomer is any one of those described above.

In accordance with the invention, the content of the polymerizable units are determined based on weight percentage of the ethylenically functionalizing vinylic monomer present in the polymerizable composition for making an intermediary copolymer relative to the total weight of polymerizable components in the polymerizable composition or the weight percentage of the ethylenically functionalizing vinylic monomer used in ethylenically functionalizing the intermediary copolymer to form the prepolymer of the invention, relative to the weight of the prepolymer.

A chain transfer agent (containing at least one thiol group) is used to control the molecular weight of the resultant intermediary copolymer. Where a chain transfer has a reactive functional group such as amine, hydroxyl, carboxyl, epoxy, isocyanate, azlactone, or aziridine group, it can provide terminal or pendant functionality (amine, hydroxyl, carboxyl, epoxy, isocyanate, azlactone, or aziridine group) for subsequent ethylenical functionalization of the resultant intermediary copolymer.

In another preferred embodiment, a polymer of the invention is a silicone hydrogel material which is obtained by thermally or actinically polymerizing a polymerizable composition which preferably comprises a TRIS-containing vinylic monomer of formula (I) as defined above and/or an actinically-crosslinkable prepolymer of the invention as described above. A silicone hydrogel material of the invention preferably is the bulk material of a soft contact lens which is obtained by polymerizing the polymerizable composition in a mold, wherein the contact lens has a water content of from about 20% to about 75% (preferably from about 25% to about 70%, more preferably from about 30% to about 65%) by weight when fully hydrated, an oxygen permeability (Dk) of at least about 40 barrers (preferably at least about 50 barrers, more preferably at least about 60 barrers, and even more preferably at least about 70 barrers), and an elastic modulus of from about 0.1 MPa to about 2.0 MPa, preferably from about 0.2 MPa to about 1.5 MPa, more preferably from about 0.3 MPa to about 1.2 MPa, even more preferably from about 0.4 MPa to about 1.0 MPa. The polymerizable composition for obtaining a soft contact lens of the invention can further comprise one or more components selected from the group consisting of a hydrophilic vinylic monomer (any one of those described above), a hydrophobic vinylic monomer (any one of those described above), a polysiloxane-containing vinylic monomer (any one of those described above), a polysiloxane-containing crosslinker (any one of those described above), a non-silicone crosslinker (any one of those described above), a photoinitiator (any one of those described above), a thermal initiator (any one of those described above), a UV-absorbing vinylic monomer (any one of those described above), a visibility tinting agent (e.g., dyes, pigments, or mixtures thereof), antimicrobial agents (e.g., preferably silver nanoparticles), a bioactive agent (e.g., rebamipide, ketotifen, olaptidine, cromoglycolate, cyclosporine, nedocromil, levocabastine, lodoxamide, ketotifen, or the pharmaceutically acceptable salt or ester thereof, 2-pyrrolidone-5-carboxylic acid, vitamins, or mixtures thereof), leachable lubricants (e.g., polyglycolic acid, a water-soluble non-crosslinkable hydrophilic polymer), leachable tear-stabilizing agents (e.g., phospholipids), and mixtures thereof.

Lens molds for making contact lenses are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

In accordance with the invention, the polymerizable composition can be introduced (dispensed) into a cavity formed by a mold according to any known methods.

After the polymerizable composition is dispensed into the mold, it is polymerized to produce a contact lens. Crosslinking may be initiated thermally or actinically, preferably by exposing the lens-forming composition in the mold to a spatial limitation of actinic radiation to crosslink the polymerizable components in the polymerizable composition.

Opening of the mold so that the molded article can be removed from the mold may take place in a manner known per se.

The molded contact lens can be subject to lens extraction to remove unpolymerized polymerizable components. The extraction solvent can be any solvent known to a person skilled in the art. Examples of suitable extraction solvent are those described above. Preferably, water or an aqueous solution is used as extraction solvent. After extraction, lenses can be hydrated in water or an aqueous solution of a wetting agent (e.g., a hydrophilic polymer).

The molded contact lenses can further subject to further processes, such as, for example, surface treatment, packaging in lens packages with a packaging solution which can contain about 0.005% to about 5% by weight of a wetting agent (e.g., a hydrophilic polymer described above or the like known to a person skilled in the art) and/or a viscosity-enhancing agent (e.g., methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof); sterilization such as autoclave at from 118 to 124° C. for at least about 30 minutes; and the like.

The invention provides, in a further aspect, a method for preparing a TRIS-containing vinylic monomer of formula (I) as defined above. A method of the invention comprises the steps of: reacting a polyoxyethylene (meth)acrylate of formula (II) with an isocyanatoalkyl tris(trimethylsiloxy)silane of formula (III)

in which $R^1$ is hydrogen or methyl, q1 is an integer of 6 to 20, and $R_2$ is an alkyl, cycloalkyl or alkylcycloalkyl (preferably alkyl) diradical with up to 20 carbon atoms which may have one or more ether, thio, amine, carbonyl, or amido linkages in the main chain (preferably, an alkyl diradical with up to 12 carbon atoms), in the presence or absence of a solvent and in the presence of a catalyst.

One known utilization of isocyanatoalkyl tris(trimethylsiloxy)silane is a cosmetic film-forming material obtained by reacting it with pullulan, as disclosed in JP-A H08-134103 (herein incorporated by reference in its entirety). However, it is unknown to start with isocyanatoalkyl tris (trimethylsiloxy)silane to produce a silicone methacrylate monomer having a desired water solubility or dispersibility and suitable for making for contact lenses.

Polyoxyethylene monomethacrylate products based on the compound of formula (II) as defined above are commercially available under the tradename of, for example, HEMA-10 (q1=10) from BIMAX Chemicals Ltd., Blemmer® PE350 (m=8) and Blemmer® PE450 (q1=10) from NOF Corp., MA-80A (q1=8) and MA-100A (q1=10) from Nippon Nyukazai Co., Ltd.

Polyoxyethylene mono-(meth)acrylate products based on the compound of formula (II) can be prepared by ring-opening polymerization reaction of ethylene oxide with hydroxyethyl (meth)acrylate ($CH_2$=CHC=$OOCH_2CH_2OH$ (HEA) or $CH_2$=$CCH_3$C=$OOCH_2CH_2OH$ (HEMA)) in the presence of an epoxy ring-opening catalyst. The product is a mixture of the desired compound (II) with polyethylene glycol (HO($CH_2CH_2O$)$_m$H) and polyoxyethylene dimethacrylate ($CH_2$=$CR^1$C=$OO(CH_2CH_2O)_{q1}$O=$CCR^1$=$CH_2$) formed as byproducts by trans-esterification during polymerization reaction. It is noted that $R^1$ is hydrogen or methyl and q1 is an integer of 6 to 20. In this context, the product is designated II', hereinafter.

The step of reacting II' with isocyanatoalkyl tris(trimethylsiloxy) silane of formula (III) (e.g., tris(trimethylsiloxy) silylpropyl isocyanate) may be carried out in a solvent although the reaction may proceed even in a solventless system. The solvent, if used, is preferably selected from ketone solvents such as methyl ethyl ketone (MEK) and methyl isobutyl ketone (MIBK).

The catalyst used for the reaction is preferably selected from amine catalysts such as triethylamine, tin catalysts such as dibutyltin dilaurate, and iron catalysts such as tris(2,4-pentanedionato)iron(III). Of these, the iron catalysts are most preferred for low toxicity because the amine compounds have a low catalytic activity and the tin catalysts are toxic despite high activity. The catalyst is preferably used in an amount of about 10 to about 1,000 ppm, more preferably about 50 to about 500 ppm based on the total weight of II' and isocyanatoalkyl tris(trimethylsiloxy) silane of formula (III).

The reacting step may be carried out by charging II', isocyanatoalkyl tris(trimethylsiloxy) silane of formula (III) (e.g., tris(trimethylsiloxy)silylpropyl isocyanate) and a reaction solvent in a reactor and adding a catalyst thereto. In the preferred procedure, a reactor is charged with II', solvent and catalyst, whereupon isocyanatoalkyl tris(trimethylsiloxy) silane of formula (III) (e.g., tris(trimethylsiloxy)silylpropyl isocyanate) is added dropwise. Preferably, dropwise addition is started at a temperature of about −10° C. to about 30° C., and the internal temperature of the reaction mixture is controlled below 50° C. during dropwise addition. The reaction temperature is preferably controlled in a range of about −10° C. to about 120° C., more preferably 20 to 50° C. On IR (infra red) monitoring, the end of reaction is detected when the peaks assigned to isocyanate group are extinguished from the IR chart. For example, the reaction is completed within about 3 hours at a reaction temperature of about 40° C. (as shown in the Examples).

For reaction, II' and isocyanatoalkyl tris(trimethylsiloxy) silane of formula (III) (e.g., tris(trimethylsiloxy)silylpropyl isocyanate) may be used in an arbitrary molar ratio. However, it is unfavorable to use isocyanatoalkyl tris(trimethylsiloxy) silane of formula (III) (e.g., tris(trimethylsiloxy) silylpropyl isocyanate) in a molar excess relative to the moles of hydroxyl groups in II' because isocyanate groups are left behind and an alcohol or the like must be added to scavenge the residual isocyanate. For this reason, II' is preferably used in such amounts that about 1.0 to about 1.2 moles of hydroxyl groups may be available per mole of isocyanatoalkyl tris(trimethylsiloxy) silane of formula (III) (e.g., tris(trimethylsiloxy)-silylpropyl isocyanate) (i.e., molar ratio of II' to isocyanatoalkyl tris(trimethylsiloxy) silane of formula (III) being from about 1.0 to about 1.2). In II', q1 is an integer of 6 to 20, preferably an integer of 8 to 14.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together. Therefore, the spirit and scope of the appended claims should not be limited to the description of the preferred versions contained therein.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

EXAMPLE 1

Oxygen Permeability Measurements.

The apparent oxygen permeability of a lens and oxygen transmissibility of a lens material is determined according to a technique similar to the one described in U.S. Pat. No. 5,760,100 and in an article by Winterton et al., (The Cornea: Transactions of the World Congress on the Cornea 111, H. D. Cavanagh Ed., Raven Press: New York 1988, pp 273-280), both of which are herein incorporated by reference in their entireties. Oxygen fluxes (J) are measured at 34° C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 $cm^3$/min., while a nitrogen stream is passed on the opposite side of the lens at a rate of about 10 to 20 $cm^3$/min. A sample is equilibrated in a test media (i.e., saline or distilled water) at the prescribed test temperature for at least 30 minutes prior to measurement but not more than 45 minutes. Any test media used as the overlayer is equilibrated at the prescribed test temperature for at least 30 minutes prior to measurement but not more than 45 minutes. The stir motor's speed is set to 1200±50 rpm, corresponding to an indicated setting of 400±15 on the stepper motor controller. The barometric pressure surrounding the system, $P_{measured}$, is measured. The thickness (t) of the lens in the area being exposed for testing is determined by measuring about 10 locations with a Mitotoya micrometer VL-50, or similar instrument, and averaging the measurements. The oxygen concentration in the nitrogen stream (i.e., oxygen which diffuses through the lens) is measured using the DK1000 instrument. The apparent oxygen permeability of the lens material, $Dk_{app}$, is determined from the following formula:

$$Dk_{app} = Jt/(P_{oxygen})$$

where J=oxygen flux [microliters $O_2$/$cm^2$-minute]

$P_{oxygen} = (P_{measured} - P_{water}$ vapor$) = $(% $O_2$ in air stream) [mm Hg]=partial pressure of oxygen in the air stream $P_{measured}$=barometric pressure (mm Hg)

$P_{water}$ vapor=0 mm Hg at 34° C. (in a dry cell) (mm Hg)

$P_{water}$ vapor=40 mm Hg at 34° C. (in a wet cell) (mm Hg)

t=average thickness of the lens over the exposed test area (mm)

$Dk_{app}$ is expressed in units of barrers.

The apparent oxygen transmissibility (Dk/t) of the material may be calculated by dividing the apparent oxygen permeability ($Dk_{app}$) by the average thickness (t) of the lens.

The above described measurements are not corrected for the so-called boundary layer effect which is attributable to the use of a water or saline bath on top of the contact lens during the oxygen flux measurement. The boundary layer effect causes the reported value for the apparent Dk of a silicone hydrogel material to be lower than the actual intrinsic Dk value. Further, the relative impact of the boundary layer effect is greater for thinner lenses than with thicker lenses. The net effect is that the reported Dk appear to change as a function of lens thickness when it should remain constant.

The intrinsic Dk value of a lens can be estimated based on a Dk value corrected for the surface resistance to oxygen flux caused by the boundary layer effect as follows.

Measure the apparent oxygen permeability values (single point) of the reference lotrafilcon A (Focus® N&D® from CIBA VISION CORPORATION) or lotrafilcon B (AirOptix™ from CIBA VISION CORPORATION) lenses using the same equipment. The reference lenses are of similar optical power as the test lenses and are measured concurrently with the test lenses.

Measure the oxygen flux through a thickness series of lotrafilcon A or lotrafilcon B (reference) lenses using the same equipment according to the procedure for apparent Dk measurements described above, to obtain the intrinsic Dk value ($Dk_i$) of the reference lens. A thickness series should cover a thickness range of approximately 100 μm or more. Preferably, the range of reference lens thicknesses will bracket the test lens thicknesses. The $Dk_{app}$ of these reference lenses must be measured on the same equipment as the test lenses and should ideally be measured contemporaneously with the test lenses. The equipment setup and measurement parameters should be held constant throughout the experiment. The individual samples may be measured multiple times if desired.

Determine the residual oxygen resistance value, $R_r$, from the reference lens results using equation 1 in the calculations.

$$R_r = \frac{\sum \left( \frac{t}{Dk_{app}} - \frac{t}{Dk_i} \right)}{n} \quad (1)$$

in which t is the thickness of the test lens (i.e., the reference lens too), and n is the number of the reference lenses measured. Plot the residual oxygen resistance value, $R_r$, vs. t data and fit a curve of the form Y=a+bX where, for the jth lens, $Y_j=(\Delta P/J)_j$ and $X=t_j$. The residual oxygen resistance, $R_r$, is equal to a.

Use the residual oxygen resistance value determined above to calculate the correct oxygen permeability $Dk_c$ (estimated intrinsic Dk) for the test lenses based on Equation 2.

$$Dk_c = t/[(t/Dk_a) - R_r] \quad (2)$$

The estimated intrinsic Dk of the test lens can be used to calculate what the apparent Dk ($Dk_{a\_std}$) would have been for a standard thickness lens in the same test environment based on Equation 3. The standard thickness ($t_{std}$) for lotrafilcon A=85 μm. The standard thickness for lotrafilcon B=60 μm.

$$Dk_{a\_std} = t_{std}/[(t_{std}/Dk_c) + R_{r\_std}] \quad (3)$$

Ion Permeability Measurements.

The ion permeability of a lens is measured according to procedures described in U.S. Pat. No. 5,760,100 (herein incorporated by reference in its entirety. The values of ion permeability reported in the following examples are relative ionoflux diffusion coefficients ($D/D_{ref}$) in reference to a lens material, Alsacon, as reference material. Alsacon has an ionoflux diffusion coefficient of $0.314 \times 10^{-3}$ $mm^2$/minute.

EXAMPLE 2

Synthesis of Monomer (1A)

A 2-L flask equipped with a Dimroth condenser, thermometer and dropping funnel is charged with 471 g (1.1 mol) of MA-80A (q1=8, Nippon Nyukazai Co., Ltd., hydroxyl number 131 mg KOH/g, polyethylene glycol/polyoxyethylene dimethacrylate/II=5/10/85), 0.09 g (100 ppm based on reactants) of tris(2,4-pentanedionato)iron(III)

as urethane-forming catalyst, and 800 g of methyl ethyl ketone as solvent. The flask is heated at 30° C. whereupon 379 g (1 mol) of tris(trimethylsiloxy)silylpropyl isocyanate is added dropwise from the dropping funnel over one hour. At this point, the internal temperature rises to 40° C. Reaction is continued at an internal temperature of 35-45° C. for 3 hours. On IR analysis, the consumption of isocyanate group is confirmed. Silica gel, 170 g, is added to the reaction solution, which is stirred for one hour for decoloring. The silica gel is filtered off, and the solvent, MEK is distilled off in vacuum at an internal temperature of 60° C., yielding 578 g of Monomer (1A) (polyoxyethylene methacrylate of formula (II) in which q1 is 8, $R_1$ is methyl, and $R_2$ is —$CH_2CH_2CH_2$—).

Synthesis of Monomer (1B)

Reaction is carried out as above for synsthsizing Monomer (1A) except that 556 g (1.1 mol) of MA-100A (q1=10, Nippon Nyukazai Co., Ltd., polyethylene glycol/polyoxyethylene dimethacrylate/II=6/14/80) was used instead of MA-80A. After decoloring, the solvent, MEK was distilled off in vacuum at 60° C., yielding 655 g of Monomer (1B) (polyoxyethylene methacrylate of formula (II) in which q1 is 10, $R_1$ is methyl, and $R_2$ is —$CH_2CH_2CH_2$—).

Characterization of TRIS-Containing Vinylic Monomer

Monomer (1A) is a colorless transparent liquid having a viscosity of 123 mm$^2$/s at 25° C., a refractive index of 1.4477 at 25° C., and a purity of 94% as determined by liquid chromatography.

Figure 1:
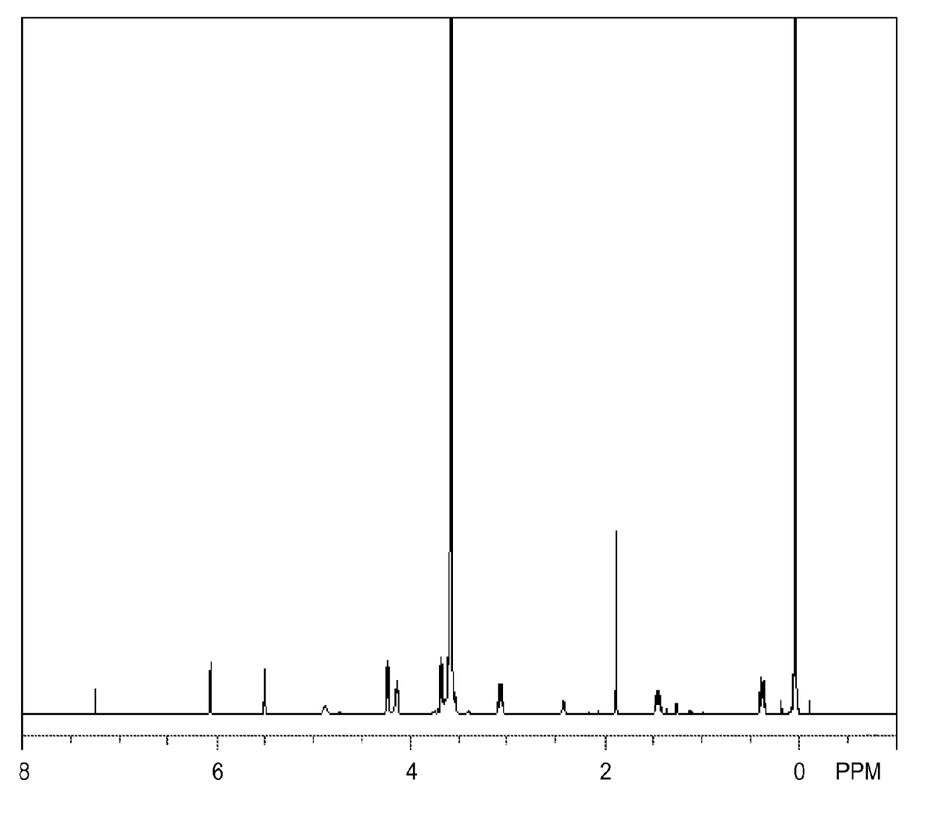
FIG. 1 is a diagram showing the $^1$H-NMR spectrum of a preferred TRIS-containing vinylic monomer.

Monomer (1B) is a colorless transparent liquid having a viscosity of 119 mm$^2$/s at 25° C., a refractive index of 1.4493 at 25° C., and a purity of 89% as determined by liquid chromatography. FIG. 1 is a diagram showing the $^1$H-NMR spectrum of Monomer (1B).

EXAMPLE 3

Synthesis of Macromers

Macromers are synthesized according to the following procedures in substantial accordance with teachings in Example B-1 to B-4 of U.S. Pat. No. 5,849,811.

51.5 g (50 mmol) of the perfluoropolyether Fomblin® ZDOL (from Ausimont S.p.A, Milan) having a mean molecular weight of 1030 g/mol and containing 1.96 meq/g of hydroxyl groups according to end-group titration is introduced into a three-neck flask together with 50 mg of dibutyltin dilaurate. The flask contents are evacuated to about 20 mbar with stirring and subsequently decompressed with argon. This operation is repeated twice. 22.2 g (0.1 mol) of freshly distilled isophorone diisocyanate kept under argon are subsequently added in a counterstream of argon. The temperature in the flask is kept below 30° C. by cooling with a waterbath. After stirring overnight at room temperature, the reaction is complete. Isocyanate titration gives an NCO content of 1.40 meq/g (theory: 1.35 meq/g).

202 g of the α,ω-hydroxypropyl-terminated polydimethylsiloxane KF-6001 from Shin-Etsu having a mean molecular weight of 2000 g/mol (1.00 meq/g of hydroxyl groups according to titration) are introduced into a flask. The flask contents are evacuated to approx. 0.1 mbar and decompressed with argon. This operation is repeated twice. The degassed siloxane is dissolved in 202 ml of freshly distilled toluene kept under argon, and 100 mg of dibutyltin dilaurate (DBTDL) are added. After complete homogenization of the solution, all the perfluoropolyether reacted with isophorone diisocyanate (IPDI) is added under argon. After stirring overnight at room temperature, the reaction is complete. The solvent is stripped off under a high vacuum at room temperature. Microtitration shows 0.36 meq/g of hydroxyl groups (theory 0.37 meq/g).

13.78 g (88.9 mmol) of 2-isocyanatoethyl methacrylate (IEM) are added under argon to 247 g of the α,ω-hydroxypropyl-terminated polysiloxane-perfluoropolyether-polysiloxane three-block copolymer (a three-block copolymer on stoichiometric average, but other block lengths are also present). The mixture is stirred at room temperature for three days. Microtitration then no longer shows any isocyanate groups (detection limit 0.01 meq/g). 0.34 meq/g of methacryl groups are found (theory 0.34 meq/g).

The macromer prepared in this way is completely colourless and clear. It can be stored in air at room temperature for several months in the absence of light without any change in molecular weight.

EXAMPLE 4

Lens formulations are prepared from the macromere prepared in Example 3, Monomer (1A) prepared in Example 2, N,N-dimethylacrylamide (DMA), solvent (1-propanol-1-PrOH or ethanol-Et-OH), photoinitiator (Darocur® 1173 from Ciba Chemicals) to have the compositions shown in Table 1. All the concentrations of the components are weight percentage (% w/w).

The photorheology of the prepared lens formulation is studied and the results are reported in Table 1.

To make lenses, a lens formulation prepared above is pipetted into dust-free contact-lens molds made from polypropylene. The molds are closed, and the polymerization reaction is effected by UV irradiation (5.0 mW/cm$^2$, 30 minutes), with simultaneous crosslinking. The molds are then opened and placed in isopropanol, causing the resultant lenses to swell out of the molds. The lenses are extracted for 4 hours minimum with 100% isopropyl alcohol before being placed into water. The lenses are coated and finally equilibrated in phosphate-buffered physiological saline solution in specially designed foil packages and then autoclaved at 120° C. for 30 minutes. The obtained lenses are characterized and the physical and mechanical properties (oxygen permeability—Dkc, ion permeability—IP, water content at equilibrium-% w/w, elastic modulus E'—Mpa, elongation at break—EtB %) are reported in Table 1.

TABLE 1

| | Formulation | |
|---|---|---|
| Components | RD-5399-073A0 | RD-5399-073A4 |
| Macromer | 31% | 29% |
| Monomer (1A) | 18% | 16% |
| DMA | 26% | 30% |
| 1-PrOH | 24% | — |
| Et-OH | — | 24% |
| DC1173 | 1% | 1% |
| Photorheology | | |
| Curing Time | 29 sec | 32 sec |
| G' | 230 kPa | 215 kPa |
| Viscosity | 16 mPa · s | 11 mPa · s |
| Lens Proeprties | | |
| Water Content % | 38.4% | 42.3% |
| Dkc | 70 | 57 |
| IP | 13 | 16 |
| E' (MPa) | 1.16 | 1.08 |
| EtB % | 165 | 78 |

What is claimed is:

1. A TRIS-containing vinylic monomer, being represented by formula (I)

in which: q1 is an integer of from 6 to 20; $R_1$ is hydrogen or methyl; $R_2$ is a diradical of an alkane or cycloalkane which comprises up to 20 carbon atoms and may have one or more ether, thio, amine, carbonyl, or amido linkages in the main chain.

2. The TRIS-containing vinylic monomer of claim 1, wherein $R_2$ is a $C_2$-$C_5$ alkane diradical.

3. The TRIS-containing vinylic monomer of claim 1, wherein the TRIS-containing vinylic monomer has a water solubility or dispersibility of at least about 5% by weight in water.

4. An actinically-crosslinkable silicone-containing prepolymer having a water solubility or dispersibility of at least about 5% by weight in water and comprising monomeric units derived from a TRIS-containing vinylic monomer of claim 1.

5. The prepolymer of claim 4, which further comprises: (1) crosslinking units derived from at least one polysiloxane-containing crosslinker and/or polysiloxane units derived from a polysiloxane-containing vinylic monomer; (2) hydrophilic units derived from at least one hydrophilic vinylic monomer; (3) polymerizable units derived from a chain transfer agent having a first reactive functional group other than thiol group and/or a vinylic monomer having a second reactive functional group other than ethylenically-unsaturated group, wherein the polymerizable units each comprise an ethylenically unsaturated group covalently attached to one polymerizable unit through the first or second reactive functional group; (4) optionally non-silicone crosslinking units derived from at least one non-silicone crosslinker; and (5) optionally UV-absorbing units derived from a UV-absorbing vinylic monomer.

6. A silicone-hydrogel material comprising hydrophilic monomeric units derived from a hydrophilic vinylic monomer and monomeric units derived from a TRIS-containing vinylic monomer of claim 1.

7. A soft contact lens comprising a silicone hydrogel material of claim 6, wherein the soft contact lens has a water content of from about 20% to about 75% by weight when fully hydrated, an oxygen permeability (Dk) of at least about 40 barrers, and an elastic modulus of from about 0.1 MPa to about 2.0 MPa.

* * * * *